United States Patent [19]

Büsser

[11] Patent Number: Plant 5,947

[45] Date of Patent: Apr. 21, 1987

[54] APPLE TREE—ELBEE

[75] Inventor: Leo Büsser, Untervaz, Switzerland

[73] Assignee: Haberli Obst- und Beerenzentrum AG, Switzerland

[21] Appl. No.: 712,562

[22] Filed: Mar. 15, 1985

[51] Int. Cl.[4] ..... A01H 5/03

[52] U.S. Cl. ..... Plt./34

[58] Field of Search ..... Plt./34

*Primary Examiner*—Robert E. Bagwill

*Attorney, Agent, or Firm*—Webb, Burden, Robinson & Webb

[57] ABSTRACT

An apple tree has the favorable qualities of the Golden Delicious with respect to production, storage and consumption. The apple, however, has a skin color of red rather than green-yellow.

4 Drawing Figures

BACKGROUND OF THE PLANT

This discovery relates to a new and distinct variety of apple tree identified by the varietal name Elbee. The new variety, which is a limb mutation of a Golden Delicious, was discovered in the discoverer's orchard in Obstgarten, Untervaz, Switzerland in the summer of 1976. The new variety appeared as a branch having red fruit on a Golden Delicious tree among a planting of young Golden Delicious trees.

The tree and its fruit were carefully observed and protected. During the course of the following year, the same red color was observed on the apple fruit of the same branch. The rest of the tree showed no variation.

The discoverer obtained several scions from this branch and grafted them on several other trees. All these graftings produced fruit with the same red color. The procedure was repeated and there are now third generation trees bearing fruit. All grafts remain stable and no retrogression or degeneration has been observed.

DESCRIPTION OF THE DRAWINGS

The accompanying photographic drawings illustrate the new variety, with color being as nearly true as color illustrations of this type.

DESCRIPTION OF THE PLANT

Figure 1:
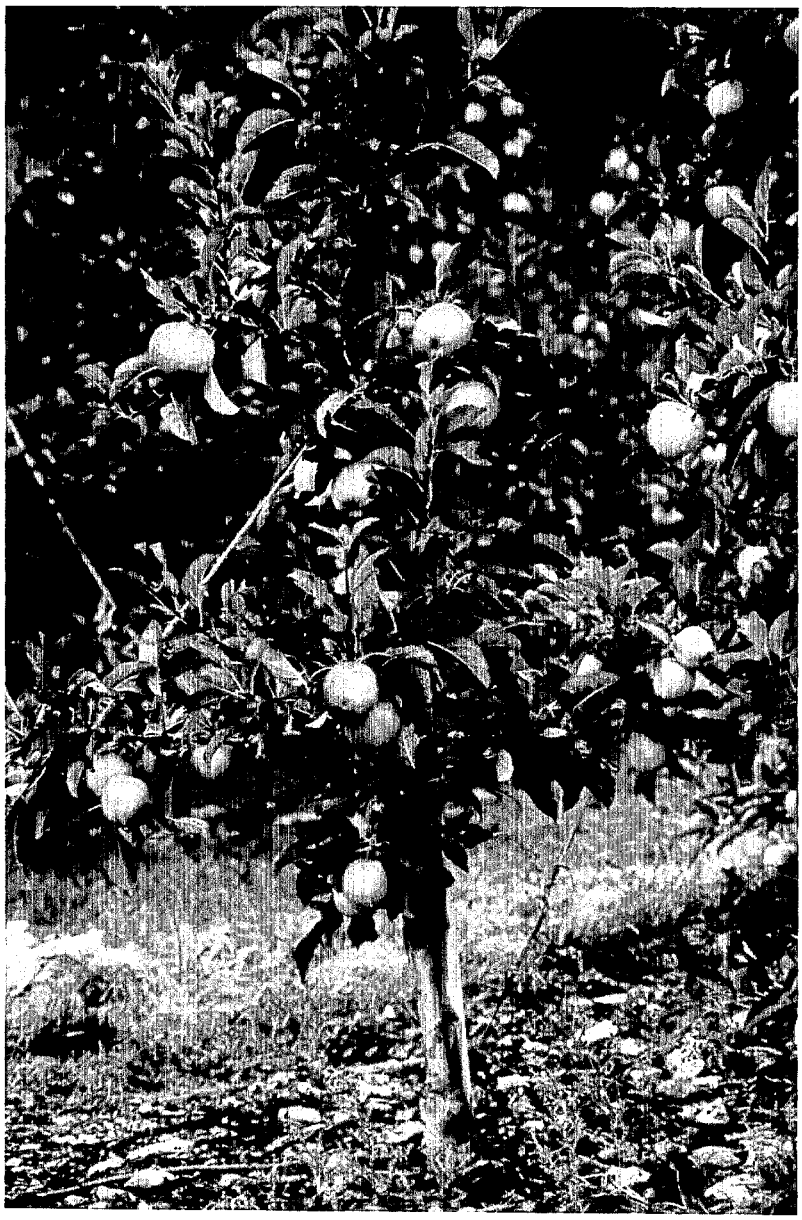
FIG. 1 is a photograph showing the new apple tree Elbee among a group of non-mutant Golden Delicious Trees.
Figure 2:
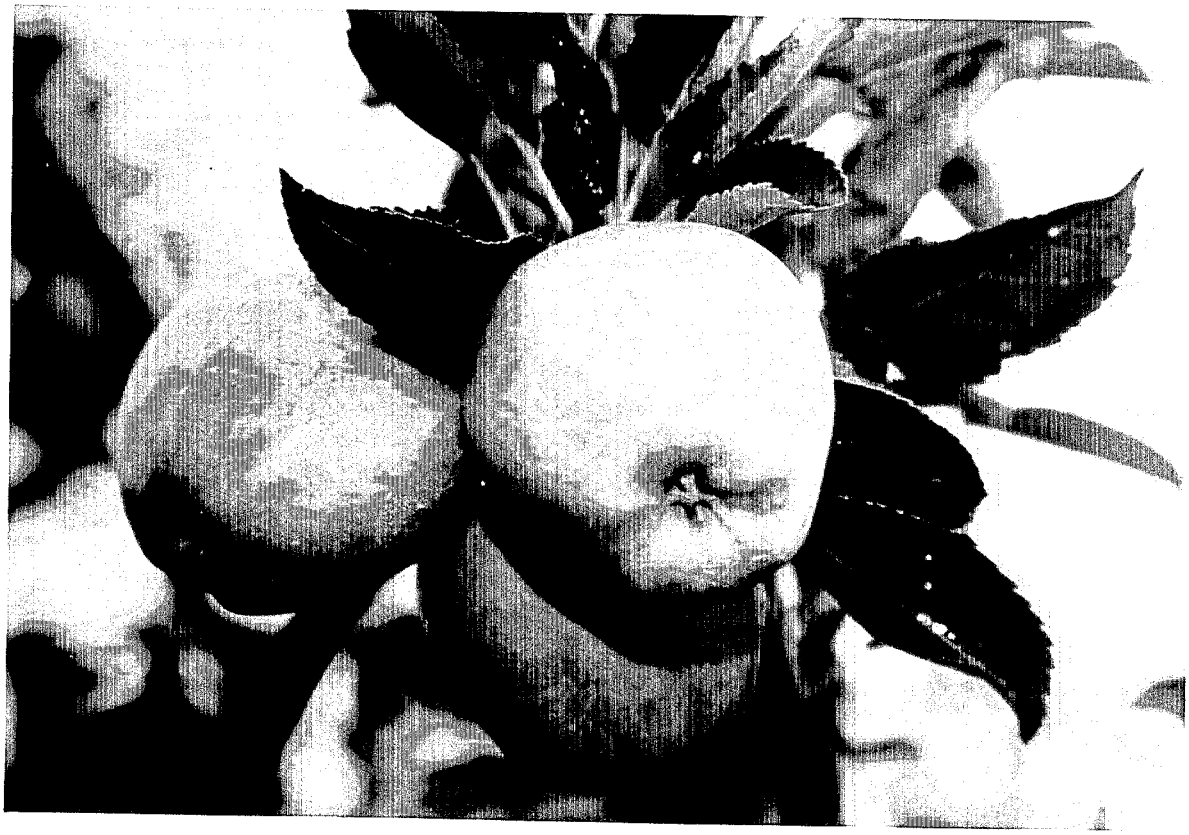
FIG. 2 is a photograph showing a fruit cluster of immature fruit.
Figure 3:
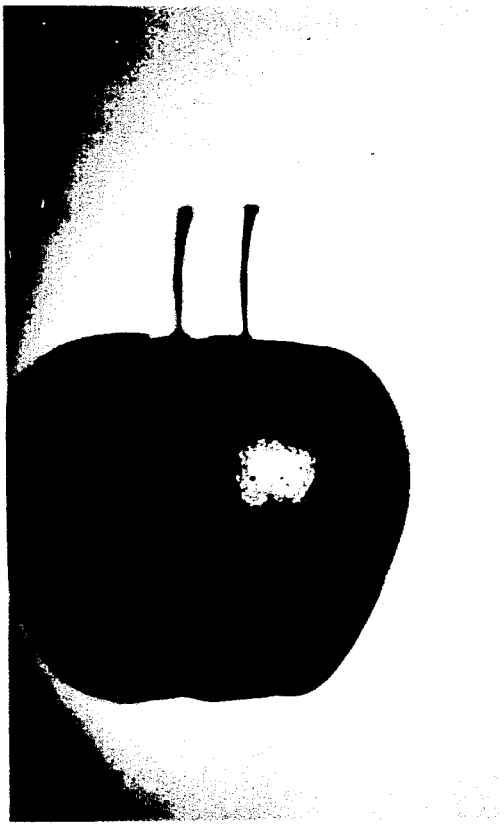
FIG. 3 and FIG. 4 are photographs showing one and two apples, respectively, of mature fruit.
Figure 4:
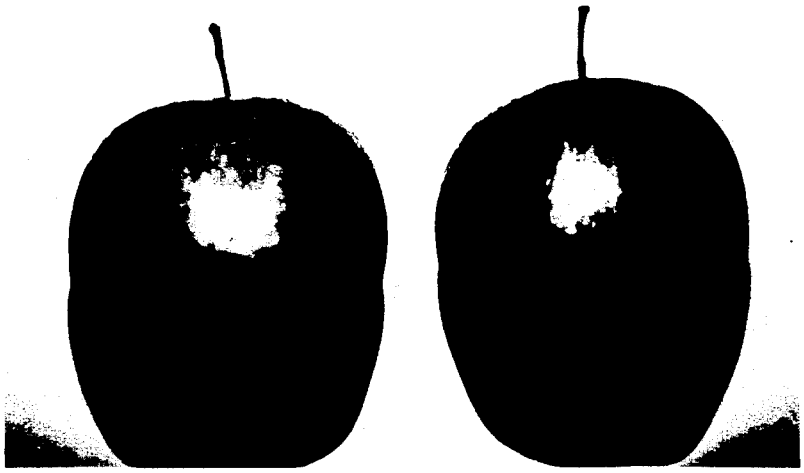

This new variety has all the known and extremely favorable qualities with respect to production, storage, and consumption of the Golden Delicious variety. As an additional characteristic, however, this new variety shows as a major feature the red color of the skin which improves the optical impression and attractiveness of the fruit and enhances its commercial value considerably.

The specimens described were grown at Untervaz, Switzerland. The color descriptions which follow refer to "Horticultural Colour Charts by the British Colour Council in Collaboration with The Royal Horticultural Society" (hereinafter R.H.S.—Horticultural Colour Charts).

Tree: Small; medium to vigorous; spreading; low; slow to medium growing; hardy; productive; very early and regular bearing; easy to trim.

Trunk: Medium; smooth.

Branches: Medium thick; smooth; much branching.

*Lenticels.*—Numerous; medium large.

Leaves: Length, 3 inches (7.6 cm); width, 1½ inches (3.8 cm); medium large; medium wide; medium long; oval; abruptly pointed; smooth. Spinach Green No. 0960 of The R.H.S.—Horticultural Colour Chart.

*Margin.*—Crenate.

Flowers: Full bloom (in Switzerland), 2 days after Golden Delicious; medium late; also flowering on one year wood; size, medium; color, white with slight pink blush on reverse side.

Fruit:

*Shape.*—Length of axis, medium; average height, about 79 mm; average breadth, about 76 mm, becoming narrower towards base, tapered near the base. Cavity of the stem is wide.

*Stem.*—Long, thin; ligneous.

*Skin.*—Smooth; dry; medium compact. Ground color, Sulphur Yellow No. ½ of The R.H.S. — Horticultural Colour Chart; changing to Reddish Buttercup Yellow No. 5/1 of The R.H.S. — Horticultural Colour Chart. Over color, Jasper Red No. 18/1 of The R.H.S. — Horticultural Colour Chart; covering 60–80% of fruit at picking time.

*Core.*—Small, with seeds well developed.

*Flesh.*—Yellowish; juicy. Texture: Firm; tender; fine cells. Flavor: Rich; harmonious; pleasant relation between sugar and acidity. Quality: Best.

*Seeds.*—Number perfect: 10. Number in one cell: 2. Length: 3/10 inch (0.8 cm). Breadth: 1/6 inch (0.45 cm). Color: Dark brown.

*Time of maturity.*—3–5 days after Golden Delicious.

*Maturity for consumption.*—Right after harvest up to July, depending on way of storage.

I claim:

1. A new and distinct variety of apple tree named Elbee and parts thereof as described and illustrated, and particularly characterized by its red fruit.

* * * * *